US011890084B2

(12) United States Patent
Park et al.

(10) Patent No.: US 11,890,084 B2
(45) Date of Patent: Feb. 6, 2024

(54) APPARATUS AND METHOD FOR ESTIMATING BIO-INFORMATION

(71) Applicant: SAMSUNG ELECTRONICS CO., LTD., Suwon-si (KR)

(72) Inventors: Chang Soon Park, Chungju-si (KR); Ui Kun Kwon, Hwaseong-si (KR); Seung Keun Yoon, Seoul (KR); Dae Geun Jang, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 478 days.

(21) Appl. No.: 17/038,692

(22) Filed: Sep. 30, 2020

(65) Prior Publication Data

US 2021/0228100 A1   Jul. 29, 2021

(30) Foreign Application Priority Data

Jan. 23, 2020   (KR) .................. 10-2020-0009152

(51) Int. Cl.
*A61B 5/024*   (2006.01)
*A61B 5/00*   (2006.01)
*A61B 5/021*   (2006.01)

(52) U.S. Cl.
CPC ...... *A61B 5/02416* (2013.01); *A61B 5/02116* (2013.01); *A61B 5/7239* (2013.01); *A61B 5/7278* (2013.01)

(58) Field of Classification Search
CPC . A61B 5/02416; A61B 5/02116; A61B 5/723; A61B 5/7278; A61B 5/02108;
(Continued)

(56) References Cited

U.S. PATENT DOCUMENTS

| 6,616,613 B1 | 9/2003 | Goodman |
| 2003/0036685 A1* | 2/2003 | Goodman .............. G16H 70/20 600/300 |

(Continued)

FOREIGN PATENT DOCUMENTS

| EP | 3 791 780 A1 | 3/2021 |
| JP | 4855721 B2 | 1/2012 |

(Continued)

OTHER PUBLICATIONS

Y. Yoon et al. :"Nonconstrained Blood Pressure Measurement by Photoplethysmography" Journal of the Optical Society of Korea, vol. 10, No. 2, Jun. 2006, (pp. 91-95).

(Continued)

*Primary Examiner* — Eric F Winakur
*Assistant Examiner* — Abid A Mustansir
(74) *Attorney, Agent, or Firm* — Sughrue Mion, PLLC

(57) ABSTRACT

An apparatus for estimating bio-information may include a sensor configured to obtain a bio-signal from an object, and a processor configured to obtain a second-order differential signal of the bio-signal, and extract a progressive wave component from the bio-signal using, based on a first local minimum point of the second-order differential signal being stable, the first local minimum point of the second-order differential signal, or extract the progressive wave component from the bio-signal using, based on the first local minimum point of the second-order differential signal being unstable, a maximum amplitude point in a systolic portion of the bio-signal.

20 Claims, 10 Drawing Sheets

(58) Field of Classification Search
CPC ... A61B 5/0205; A61B 5/0002; A61B 5/0006; A61B 5/02007; A61B 5/02438; A61B 5/029; A61B 5/6802; A61B 5/6803; A61B 5/681; A61B 5/746; A61B 5/7275; A61B 5/0075

See application file for complete search history.

(56) References Cited

U.S. PATENT DOCUMENTS

| | | |
|---|---|---|
| 2007/0016085 A1 | 1/2007 | Inukai et al. |
| 2016/0135692 A1* | 5/2016 | Lisogurski ............. A61B 5/318 600/324 |
| 2016/0270668 A1 | 9/2016 | Gil |
| 2018/0098731 A1* | 4/2018 | Yoon ...................... A61B 5/318 |
| 2019/0076099 A1 | 3/2019 | Park et al. |
| 2019/0110757 A1 | 4/2019 | Kwon et al. |
| 2021/0068762 A1 | 3/2021 | Park et al. |

FOREIGN PATENT DOCUMENTS

| | | |
|---|---|---|
| JP | 2017192607 A | 10/2017 |
| JP | 2019-058653 A | 4/2019 |
| KR | 10-1503604 B1 | 3/2015 |
| KR | 10-2019-0029889 A | 3/2019 |

OTHER PUBLICATIONS

Sandrine C. Millasseau et al. "The Vascular Impact of Aging and Vasoactive Drugs: Comparison of Two Digital Volume Pulse Measurements" American Journal of Hypertension, vol. 16, No. 6, Jun. 2003, (pp. 467-472).

Martin C Baruch et al. "Validation of the pulse decomposition analysis algorithm using central arterial blood pressure" BioMedical Engineering Online, 2014 (pp. 1-19).

Communication dated Jun. 11, 2021 by the European Patent Office in counterpart European Patent Application No. 20216581.7.

* cited by examiner

APPARATUS AND METHOD FOR ESTIMATING BIO-INFORMATION

CROSS-REFERENCE TO RELATED APPLICATION(S)

This application is based on and claims priority under 35 U.S.C. § 119 to Korean Patent Application No. 10-2020-0009152, filed on Jan. 23, 2020, in the Korean Intellectual Property Office, the disclosure of which is incorporated by reference herein in its entirety.

BACKGROUND

1. Field

The disclosure relates to an apparatus and method for non-invasively estimating bio-information.

2. Description of Related Art

Recently, with the aging population, soaring medical costs, and a lack of medical personnel for specialized medical services, research is being actively conducted on information technology (IT)-medical convergence technologies, in which IT and medical technology are combined. Particularly, monitoring of the health condition of the human body is not limited to medical institutions, but is expanding to mobile healthcare fields that may monitor a user's health condition anywhere and anytime in daily life at the home or office. Typical examples of bio-signals, which indicate the health condition of individuals, include an electrocardiography (ECG) signal, a photoplethysmogram (PPG) signal, an electromyography (EMG) signal, and the like, and various bio-signal sensors have been developed to measure these signals in daily life. Particularly, a PPG sensor may estimate blood pressure of a human body by analyzing a shape of pulse waves which reflect cardiovascular status, and the like.

According to studies on the PPG signal, the entire PPG signal is a superposition of a propagation wave departing from the heart and moving toward the distal portions of the body, and reflection waves returning from the distal portions. Further, it has been known that information for estimating blood pressure may be obtained by extracting various features associated with the propagation wave or the reflection waves.

SUMMARY

Additional aspects will be set forth in part in the description which follows and, in part, will be apparent from the description, or may be learned by practice of the presented embodiments.

According to an aspect of an example embodiment, an apparatus for estimating bio-information may include a sensor configured to obtain a bio-signal from an object, and a processor configured to obtain a second-order differential signal of the bio-signal, and extract a progressive wave component from the bio-signal using, based on a first local minimum point of the second-order differential signal being stable, the first local minimum point of the second-order differential signal, or extract the progressive wave component from the bio-signal using, based on the first local minimum point of the second-order differential signal being unstable, a maximum amplitude point in a systolic portion of the bio-signal.

The sensor may include a pulse wave sensor including a light source configured to emit light onto the object, and a detector configured to detect light reflected by or scattered from the object.

The processor may determine whether an inflection point exists in a detection period of the second-order differential signal; and determine whether the first local minimum point is stable based on whether the inflection point exists in the detection period of the second-order differential signal.

The detection period may include a time interval between a first local maximum point and the first local minimum point of the second-order differential signal.

The inflection point is a point at which a waveform of the second-order differential signal changes from being convex downward to convex upward.

The processor may obtain a fourth-order differential signal of the bio-signal; detect a first point, which satisfies a condition that an amplitude at the first point is greater than zero and an amplitude at a second point is less than zero, in a detection period of the fourth-order differential signal; and detect a point, corresponding to the first point, as the inflection point from the second-order differential signal.

Based on determining that the first local minimum point is stable, the processor may extract the progressive wave component based on the first local minimum point of the second-order differential signal.

The processor may extract, as the progressive wave component, at least one of an amplitude of the bio-signal, which corresponds to a time of the first local minimum point, and an amplitude of the bio-signal which corresponds to an internally dividing point between the time of the first local minimum point and a time of a second local maximum point of the second-order differential signal.

Based on determining that the first local minimum point is unstable, the processor may detect the maximum amplitude point in the systolic portion of the bio-signal, and extract the progressive wave component based on the detected maximum amplitude point.

The processor may extract, as the progressive wave component, at least one of an amplitude of the maximum amplitude point, and an amplitude of the bio-signal which corresponds to an internally dividing point between a time of the inflection point, which is detected in the detection period of the second-order differential signal, and a time of the maximum amplitude point.

The processor may estimate the bio-information based on the extracted progressive wave component.

The bio-information may include at least one of blood pressure, vascular age, arterial stiffness, aortic pressure waveform, stress index, and fatigue level.

According to an aspect of an example embodiment, a method of estimating bio-information may include obtaining a bio-signal from an object; obtaining a second-order differential signal of the bio-signal; determining whether a first local minimum point of the second-order differential signal is stable; and extracting a progressive wave component from the bio-signal using, based on determining that the first local minimum point of the second-order differential signal is stable, the first local minimum point of the second-order differential signal, or extracting the progressive wave component from the bio-signal using, based on determining that the first local minimum point of the second-order differential signal is unstable, a maximum amplitude point in a systolic portion of the bio-signal The determining whether the first local minimum point of the second-order differential signal is stable may include determining whether an inflection point exists in a detection period of the second-order differential signal; and determining whether the first local minimum point is stable based on whether the inflection point exists in the detection period of the second-order differential signal.

The detection period may include a time interval between a first local maximum point and the first local minimum point of the second-order differential signal.

The inflection point may be a point at which a waveform of the second-order differential signal changes from being convex downward to convex upward.

The method may include obtaining a fourth-order differential signal of the bio-signal; detecting a first point, which satisfies a condition that an amplitude at the first point is greater than zero and an amplitude at a second point is less than zero, in a detection period of the fourth-order differential signal; and detecting a point, corresponding to the first point, as the inflection point from the second-order differential signal.

The extracting of the progressive wave component may include, in response to determining that the first local minimum point is stable, extracting the progressive wave component based on the first local minimum point of the second-order differential signal.

The extracting of the progressive wave component may include, in response to determining that the first local minimum point is stable, extracting, as the progressive wave component, at least one of an amplitude of the bio-signal, which corresponds to a time of the first local minimum point, and an amplitude of the bio-signal which corresponds to an internally dividing point between the time of the first local minimum point and a time of a second local maximum point of the second-order differential signal.

The extracting of the progressive wave component may include, in response to determining that the first local minimum point is unstable, extracting the maximum amplitude point in the systolic portion of the bio-signal; and extracting the progressive wave component based on the detected maximum amplitude point.

The extracting of the progressive wave component based on the detected maximum amplitude point may include extracting, as the progressive wave component, at least one of an amplitude of the maximum amplitude point, and an amplitude of the bio-signal which corresponds to an internally dividing point between a time of the inflection point, which is detected in the detection period of the second-order differential signal, and a time of the maximum amplitude point.

The method may include estimating the bio-information based on the extracted progressive wave component.

BRIEF DESCRIPTION OF THE DRAWINGS

The above and other aspects, features, and advantages of certain embodiments of the present disclosure will be more apparent from the following description taken in conjunction with the accompanying drawings, in which.

Figure 1:
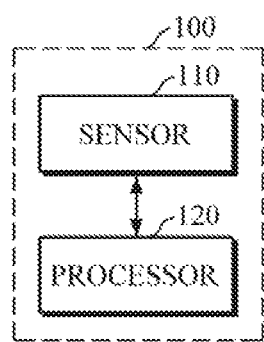
FIG. 1 is a block diagram illustrating an apparatus for estimating bio-information according to an embodiment.

Throughout the drawings and the detailed description, unless otherwise described, the same drawing reference numerals will be understood to refer to the same elements, features, and structures. The relative size and depiction of these elements, features, and structures may be exaggerated for clarity, illustration, and convenience.

DETAILED DESCRIPTION

Details of the embodiments are included in the following detailed description and drawings. Advantages and features of the present disclosure, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms "first," "second," etc., may be used herein to describe various elements, these elements should not be limited by these terms. These terms are only used to distinguish one element from another. Any references to the singular form of a term may include the plural form of the term unless expressly stated otherwise. In addition, unless explicitly described to the contrary, an expression such as "comprising" or "including" will be understood to imply the inclusion of the stated elements, but not the exclusion of any other elements. Also, terms such as "part," "module," etc., should be understood as a unit for performing at least one function or operation, and that may be embodied as hardware, software, or a combination thereof.

Hereinafter, embodiments of an apparatus and method for estimating bio-information will be described in detail with reference to the accompanying drawings.

FIG. 1 is a block diagram illustrating an apparatus for estimating bio-information according to an embodiment of the present disclosure. The apparatus 100 for estimating bio-information may be embedded in a terminal, such as a smartphone, a tablet personal computer (PC), a desktop computer, a laptop computer, and the like, or may be manufactured as an independent hardware device. In this case, if the apparatus 100 for estimating bio-information is manufactured as an independent hardware device, the device may be a wearable device worn on an object OBJ to allow a user to easily measure bio-information while carrying the device. Examples of the wearable device may include a wristwatch-type wearable device, a bracelet-type wearable device, a wristband-type wearable device, a ring-type wearable device, a glasses-type wearable device, a headband-type wearable device, or the like, but the wearable device is not limited thereto, and may be modified for various purposes, such as a fixed type device and the like used in medical institutions for measuring and analyzing bio-information.

Referring to FIG. 1, the apparatus 100 for estimating bio-information includes a sensor 110 and a processor 120.

As illustrated in FIG. 1, the sensor 110 may obtain a bio-signal from an object OBJ, and may transmit the obtained bio-signal to the processor 120. In this case, the bio-signal may include a PPG signal (hereinafter referred to as a "pulse wave signal"). However, the bio-signal is not limited thereto, and may include various bio-signals, such as an ECG signal, a PPG signal, an EMG signal, and the like, which may be modeled by a sum of a plurality of waveform components.

For example, the sensor 110 may include a PPG sensor for measuring the PPG signal. The PPG sensor may include a light source for emitting light onto the object, and a detector for measuring the PPG signal by detecting light emanating from the object when light, emitted by the light source onto the object, is scattered or reflected from body tissue of the object. In this case, the light source may include at least one of a light-emitting diode (LED), a laser diode (LD), and a phosphor, but is not limited thereto. The detector may include a photo diode.

Based on receiving a control signal from the processor 120, the sensor 110 may drive the PPG sensor to obtain a pulse wave signal from the object. In this case, the object may be a body part which comes into contact with or is adjacent to the PPG sensor, and may be a body part where pulse waves may be easily measured using photoplethysmography. For example, the object may be an area on the wrist that is adjacent to the radial artery, and may include an upper portion of the wrist where veins or capillaries are located. In the case where the pulse waves are measured on an area of skin where the radial artery passes, measurement may be relatively less affected by external factors, such as the thickness of skin tissue in the wrist, and the like, which may cause errors in measurement. However, the skin area is not limited thereto, and may be distal portions of the body, such as fingers, toes, and the like, where blood vessels are densely located.

Based on receiving a request for estimating bio-information from a user, the processor 120 may generate a control signal for controlling the sensor 110, and may transmit the control signal to the sensor 110. Further, the processor 120 may receive a bio-signal from the sensor 110, and may estimate bio-information by analyzing the received bio-signal. In this case, bio-information may include blood pressure, vascular age, arterial stiffness, aortic pressure waveform, stress index, fatigue level, and the like, but is not limited thereto.

Based on receiving the bio-signal from the sensor 110, the processor 120 may perform preprocessing, such as filtering for removing noise, amplifying the bio-signal, converting the signal into a digital signal, and the like.

The processor 120 may extract features, for estimating bio-information, by analyzing a waveform of the received bio-signal. For example, the processor 120 may obtain individual pulse waveform components, which constitute the waveform of the bio-signal, and may obtain features by using the obtained pulse waveform components or by combining the pulse waveform components with other additional information.

As will be described in detail below with reference to FIG. 3, the processor 120 may obtain the individual pulse waveform components by analyzing a second-order differential signal of the bio-signal. The processor 120 may obtain, as a progressive wave component, a time of a first local minimum point of the second-order differential signal, and/or an amplitude of the bio-signal which corresponds to the time, and may obtain features by using the obtained progressive wave component.

However, a bio-signal having a non-ideal waveform shape may be generated due to noise in the measurement of the bio-signal, a non-ideal contact state of the human body, an unusual condition of a subject, and the like. In the bio-signal obtained under these circumstances, a first local minimum point may not be detected at a location, at which the first local minimum point is originally desired to be detected from the second-order differential signal, or the first local minimum point may not be detected clearly. In order to extract features stably even in these various circumstances, the processor 120 may determine whether the waveform of the bio-signal, particularly the first local minimum point of the second-order differential signal, is stable and may adaptively obtain the progressive wave component based on the determination.

Figure 2:
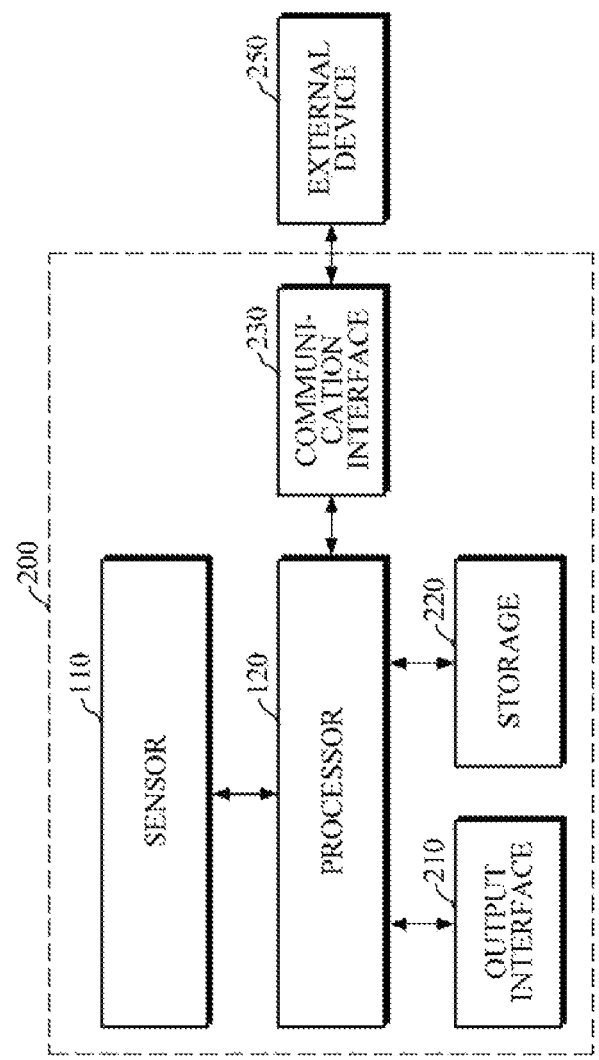
FIG. 2 is a block diagram illustrating an apparatus for estimating bio-information according to another embodiment.

FIG. 2 is a block diagram illustrating an apparatus for estimating bio-information according to another embodiment of the present disclosure.

Referring to FIG. 2, the apparatus 200 for estimating bio-information includes a sensor 110, a processor 120, an output interface 210, a storage 220, and a communication interface 230.

The sensor 110 may measure a bio-signal from an object, and the processor 120 may estimate bio-information by using the bio-signal measured by the sensor 110.

The output interface 210 may output bio-signal information, measured by the sensor 110, and various processing results of the processor 120, and may provide the output information for a user. The output interface 210 may provide the information by various visual/non-visual methods using a display module, a speaker, a haptic device, and the like, which are mounted in the apparatus 200 for estimating bio-information.

For example, based on a user's blood pressure being estimated, the output interface 210 may output the estimated blood pressure by using various visual methods, such as by changing color, line thickness, font, and the like, based on whether the estimated blood pressure value falls within or outside of a normal range. Alternatively, the output interface 210 may output the estimated blood pressure by voice, or may output the estimated blood pressure using non-visual methods by providing different vibrations or tactile sensations and the like, according to abnormal blood pressure levels. In addition, based on comparing the measured blood pressure with a previous measurement history, if it is determined that the measured blood pressure is abnormal, the output interface 210 may warn a user, or may provide guide information on a user's action such as food information that the user should be careful about, information for booking a hospital appointment, and the like.

The storage 220 may store a variety of reference information for estimating bio-information, obtained bio-signals, detected characteristic points, extracted features, bio-information estimation results, and the like. In this case, the variety of reference information for estimating bio-information may include user information, such as a user's age, sex, occupation, current health condition, and the like, information on a bio-information estimation model, and the like, but the reference information is not limited thereto.

For example, the storage 220 may include at least one storage medium of a flash memory type memory, a hard disk type memory, a multimedia card micro type memory, a card type memory (e.g., a secure digital (SD) memory, an extreme digital (XD) memory, etc.), a Random Access Memory (RAM), a Static RAM (SRAM), a Read-Only Memory (ROM), an Electrically Erasable Programmable ROM (EEPROM), a Programmable ROM (PROM), a magnetic memory, a magnetic disk, and an optical disk, and the like, but is not limited thereto.

Based on receiving a control signal, including access information of an external device 250, from the processor 120, the communication interface 230 may access a communication network using communication techniques to connect to the external device 250. Based on connecting to the external device 250, the communication interface 230 may receive a variety of information related to estimating bio-information from the external device 250, and may transmit the bio-signal measured by the sensor 110, the bio-information estimated by the processor 120, and the like, to the external device 250. In this case, examples of the external device 250 may include another apparatus for estimating bio-information, a cuff manometer for measuring cuff blood pressure and the like, a smartphone, a tablet PC, a desktop computer, a laptop computer, and the like, but the external device 250 is not limited thereto.

In this case, examples of the communication techniques ay include Bluetooth communication, Bluetooth Low Energy (BLE) communication, Near Field Communication (NFC), wireless local area network (WLAN) communication, Zigbee communication, Infrared Data Association (IrDA) communication, wireless fidelity (Wi-Fi) Direct (WFD) communication, Ultra-Wideband (UWB) communication, Ant+ communication, Wi-Fi communication, and mobile communication. However, this is merely exemplary and is not intended to be limiting.

Figure 3:
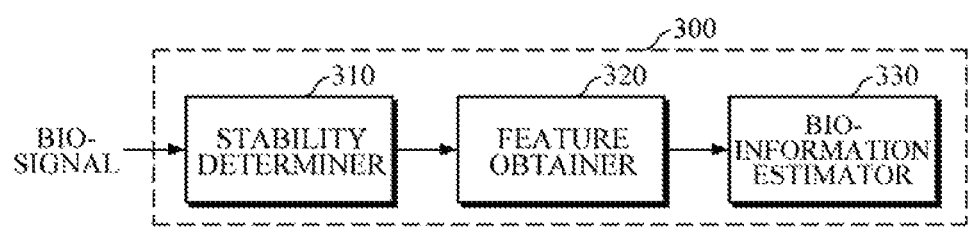
FIG. 3 is a block diagram illustrating a processor according to the embodiments of FIGS. 1 and 2.

FIG. 3 is a block diagram illustrating a processor according to the embodiments of FIGS. 1 and 2. FIGS. 4A to 4D are diagrams explaining examples of extracting a progressive wave component from a bio-signal.

Referring to FIG. 3, a processor 300 includes a stability determiner 310, a feature obtainer 320, and a bio-information estimator 330.

Figure 4A:
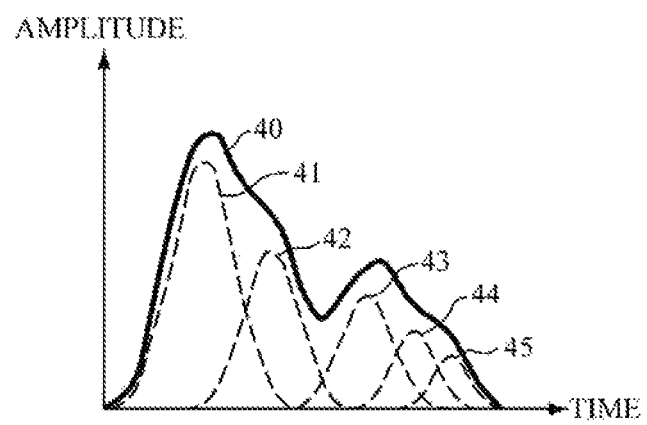
FIGS. 4A to 4D are diagrams explaining examples of extracting a progressive wave component from a bio-signal according to an embodiment.

FIG. 4A is a diagram illustrating a waveform of a pulse wave signal 40 which is constituted by a superposition of five constituent pulses 41, 42, 43, 44, and 45. By combining time and amplitude information associated with each of the constituent pulses 41, 42, 43, 44, and 45 of the pulse wave signal 40, features having a high correlation with blood pressure may be obtained. Generally, pulses up to the third constituent pulse are mainly used to estimate blood pressure, and particularly the first constituent pulse waveform component may be extracted as a component associated with the progressive wave. Pulses after the third pulse may not be observed depending on individuals in some cases, and are difficult to be found due to noise or have a low correlation with estimation of blood pressure.

In an ideal bio-signal, an upward convex shape may be clearly shown at each time point of the constituent pulse waveform components, as illustrated FIG. 4A. However, due to noise in the measurement of the bio-signal, an abnormal contact of an object with the sensor 110, or unusual characteristics of a user's object, e.g., unusual vascular structure, and the like, a non-ideal waveform shape may be generated. Alternatively, in the case where a bio-signal is measured from a portion of capillaries rather than arteries, high frequency components mostly disappear and only low frequency components remain, thereby producing a smooth waveform of the bio-signal.

In order to obtain features stably from the bio-signal measured in these various circumstances, the stability determiner 310 may determine whether the waveform of the bio-signal is stable. For example, in order to adaptively obtain the progressive wave component based on the stability of the waveform of the bio-signal, the stability determiner 310 may obtain a second-order differential signal of the bio-signal measured by the sensor 110, and may determine whether the first local minimum point of the second-order differential signal is stable, which is related to the progressive wave component.

For example, the stability determiner 310 may detect an inflection point in a detection period of the second-order differential signal, and may determine whether the first local minimum point is stable based on the presence of the inflection point. In this case, the detection period may include a time interval between a first local maximum point and the first local minimum point of the second-order differential signal, and may be adjusted by considering device performance, speed, and the like.

If there is no inflection point in the detection period of the second-order differential signal, the stability determiner 310 may determine that the first local minimum point is stable. Alternatively, if there is ana inflection point in the detection period, the stability determiner 310 may determine that the first local minimum point is unstable. In this case, the inflection point may be a point, at which a waveform of the second-order differential signal changes from being convex "downward" to convex "upward" in the detection period of the second-order differential signal.

The stability determiner 310 may obtain a fourth-order differential signal by, for example, performing fourth-order differentiation on the bio-signal, and may detect an inflection point by using the fourth-order differential signal. The stability determiner 310 may detect a first point, which satisfies a condition that an amplitude at the first point t is greater than 0 and an amplitude at a second point t+1 after the first point t is less than 0, in a detection period of the fourth-order differential signal, and the stability determiner 310 may detect a point, corresponding to the first point t, as an inflection point from the second-order differential signal.

The feature obtainer 320 may adaptively obtain a progressive wave component based on the determination of the stability determiner 310, and may obtain features by using the obtained progressive wave component.

Figure 4B:
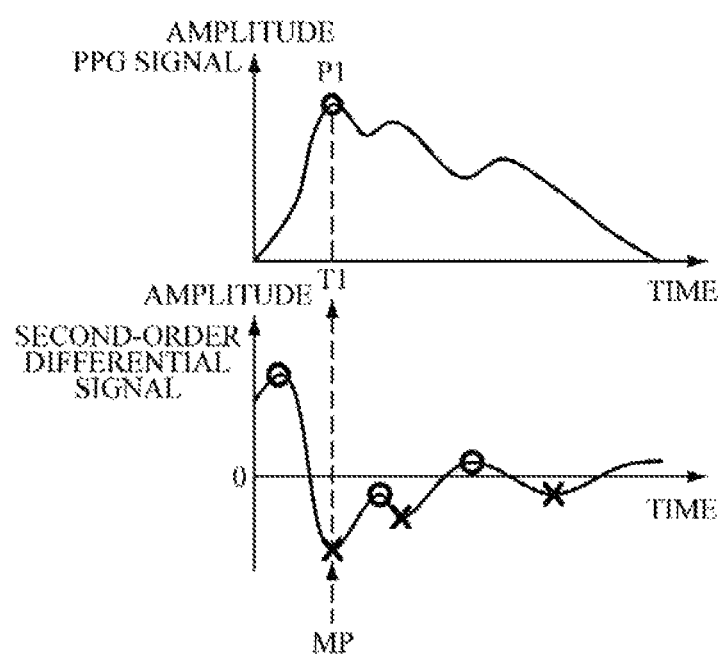

FIG. 4B is a diagram illustrating a case in which the stability determiner 310 determines that the first local minimum point is stable, i.e., a case in which an inflection point is not detected in the detection period of the second-order differential signal.

In response to a determination that the first local minimum point is stable, the feature obtainer 320 may obtain a progressive wave component based on the first local minimum point MP of the second-order differential signal. For example, the feature obtainer 320 may detect the first local minimum point MP of the second-order differential signal, and may obtain an amplitude P1 of the bio-signal, which corresponds to a time T1 of the first local minimum point, as the progressive wave component. In another example, the feature obtainer 320 may obtain an internally dividing point between the time of the first local minimum point and a time of a second local maximum point of the second-order differential signal, and may obtain an amplitude of the bio-signal, which corresponds to the internally dividing point, as the progressive wave component. In this case, the feature obtainer 320 may apply a weight to each of the first local minimum point and the second local maximum point. However, the feature is not limited thereto, and the feature obtainer 320 may obtain a value having a predetermined ratio to the amplitude P1 at the first local minimum point MP, a value having a predetermined ratio to the time T1 at the first local minimum point MP, or an amplitude at a time point obtained by adding or subtracting a predetermined value to or from the time T1, as the progressive wave component.

Figure 4C:
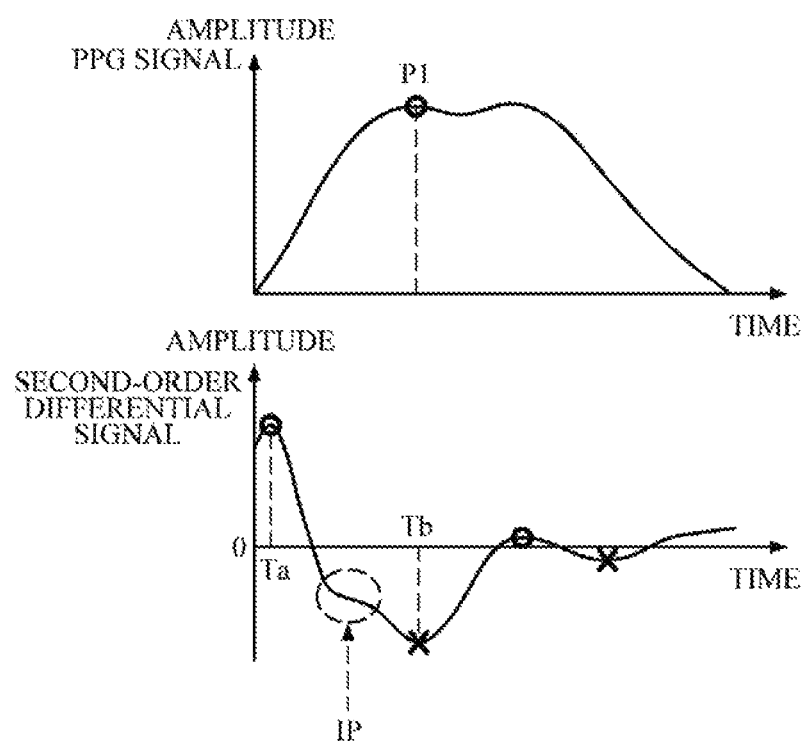

FIG. 4C is a diagram illustrating a case in which the stability determiner 310 determines that the first local minimum point is unstable, i.e., a case in which an inflection point is detected in the detection period.

The stability determiner 310 may detect an inflection point IP in the detection period of the second-order differential signal (lower view of FIG. 4C), e.g., an interval between a time Ta of a first local maximum point and a time Tb of a first local minimum point, and if there is the inflection point IP, the stability determiner 310 may determine that the first local minimum point is unstable. In other words, the first local minimum point appears at a point, which is detected as the inflection point IP, in normal circumstances, but if the first local minimum point is not detected clearly at the point, is transformed into an inflection point, and then the first local minimum point is detected thereafter, the stability determiner 310 may determine that the first local minimum point, which is actually detected from the second-order differential signal, is unstable.

Based on detecting the inflection point IP, the feature obtainer 320 may detect a maximum amplitude point Pmax in a systolic portion of the bio-signal and may obtain a progressive wave component based on the maximum amplitude point Pmax, without using the first local minimum point, actually detected from the second-order differential signal, as the progressive wave component. In this case, the systolic portion may refer to an interval from a start point of the bio-signal to a dicrotic notch point.

Figure 4D:
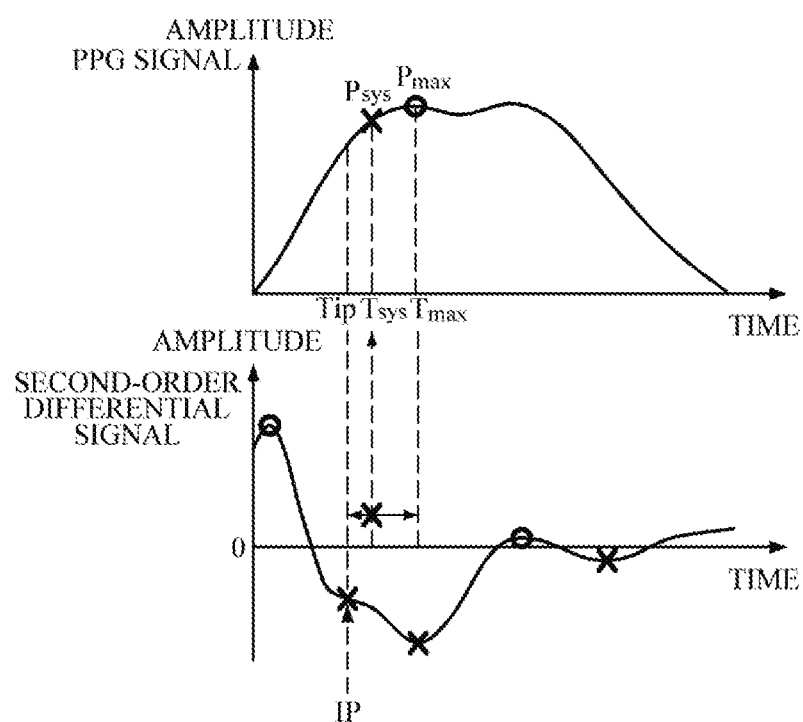

For example, as illustrated in FIG. 4C, the feature obtainer 320 may obtain an amplitude value at the maximum amplitude point Pmax of the bio-signal as the progressive wave component. In another example, as illustrated in FIG. 4D, the feature obtainer 320 may obtain an internally dividing point between a time Tip of the detected inflection point IP and a time Tmax of the maximum amplitude point Pmax, and may obtain an amplitude Psys, which corresponds to the time Tsys of the internally dividing point, as the progressive wave component. In this case, a pre-defined weight may be applied to each of the time Tip of the inflection point IP and the time Tmax of the maximum amplitude point Pmax. However, the feature is not limited thereto, and the feature obtainer 320 may obtain a value having a predetermined ratio to the amplitude at the maximum amplitude point Pmax, a value having a predetermined ratio to the time Tmax at the maximum amplitude point Pmax, or an amplitude at a time point obtained by adding or subtracting a predetermined value to or from the time Tmax, as the progressive wave component.

Based on adaptively obtaining the progressive wave component, the feature obtainer 320 may obtain features for estimating bio-information by using the progressive wave component. For example, the feature obtainer 320 may obtain, as features, the progressive wave component, i.e., the amplitude value itself, or a value obtained by processing the amplitude value. For example, by using various methods including adding or subtracting a predetermined value to or from the amplitude value, or multiplying or dividing the amplitude value by a predetermined value, the feature obtainer 320 may process the progressive wave component based on a type of bio-information, a user's unusual condition, and the like.

Alternatively, the feature obtainer 320 may extract a variety of additional information from the bio-signal, and may obtain features by properly combining the extracted additional information and the progressive wave component. For example, by using the second-order differential signal, the feature obtainer 320 may obtain, as additional information, amplitude values of the bio-signal which correspond to a second local minimum point and a third local minimum point, a maximum amplitude value in the systolic portion of the bio-signal, a total or partial area of the bio-signal, and the like.

Based on the feature obtainer 320 extracting the features, the bio-information estimator 330 may estimate bio-information by using the extracted features. The bio-information estimator 330 may estimate bio-information from the extracted features by applying a predetermined bio-information estimation model. In this case, the bio-information estimation model may be expressed in the form of a linear or non-linear function which defines a correlation between the features and bio-information, e.g., blood pressure.

Figure 5:
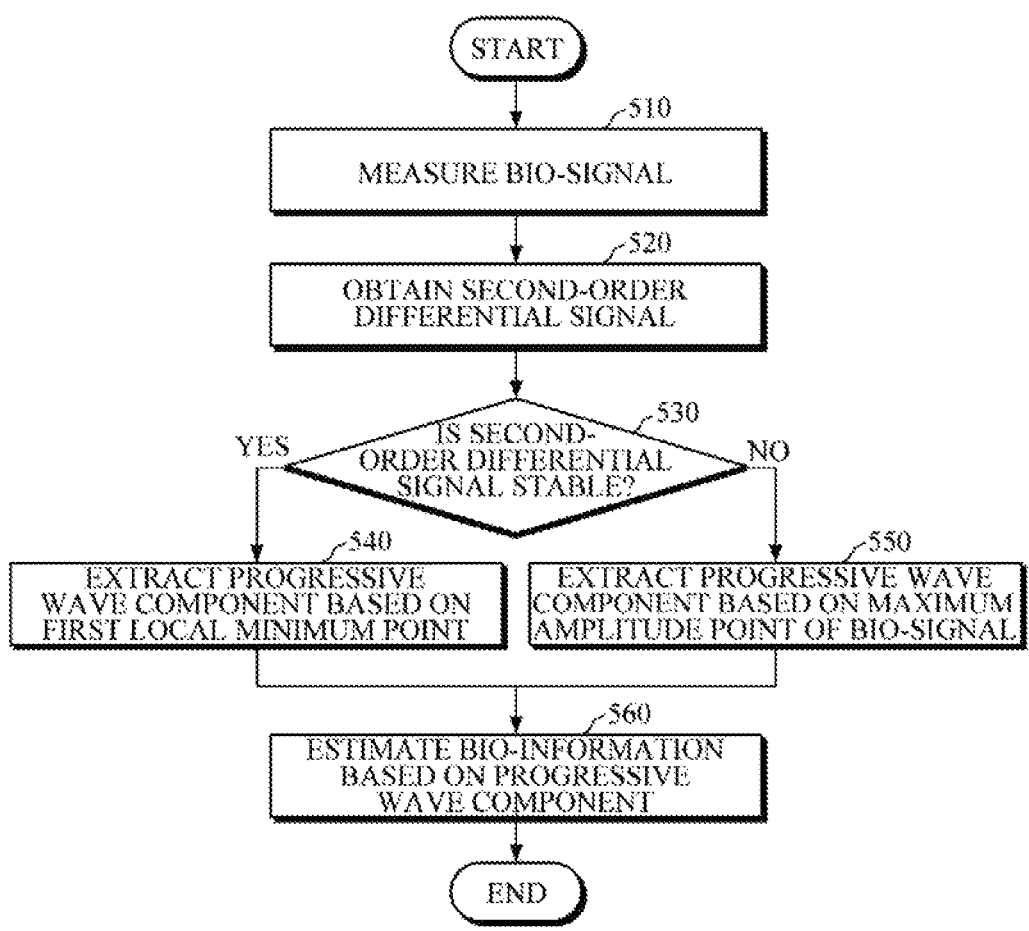
FIG. 5 is a flowchart illustrating a method of estimating bio-information according to an embodiment.

FIG. 5 is a flowchart illustrating a method of estimating bio-information according to an embodiment of the present disclosure.

The method of FIG. 5 is an example of a method of estimating bio-information which is performed by the apparatuses 100 and 200 for estimating bio-information.

Based on receiving a request for estimating bio-information, the apparatuses 100 and 200 for estimating bio-information may measure a bio-signal from a user's object in operation 510.

The apparatuses 100 and 200 for estimating bio-information may provide an interface for various interactions with a user, and may receive the request for estimating bio-information from the user through the provided interface. Alternatively, the apparatuses 100 and 200 for estimating bio-information may receive a request for estimating bio-information from an external device. In this case, the request for estimating bio-information of the external device may include a request for providing a bio-information estimation result. In the case where the external device includes a bio-information estimation algorithm, the request for estimating bio-information may also include a request for providing feature information. The external device may be a smartphone, a tablet PC, and the like which may be carried by the user.

Then, the apparatuses 100 and 200 for estimating bio-information may obtain a second-order differential signal of the bio-signal in operation 520, and may determine whether the second-order differential signal, particularly a first local minimum point of the second-order differential signal, is stable in operation 530.

For example, the apparatuses 100 and 200 for estimating bio-information may detect whether an inflection point exists in a detection period of the second-order differential signal. If there is no inflection point, then the apparatuses 100 and 200 for estimating bio-information may determine that the first local minimum point is stable. Alternatively, if there is an inflection point, then the apparatuses 100 and 200 for estimating bio-information may determine that the first local minimum point is unstable. In this case, the inflection point may be a point, at which a waveform of the second-order differential signal changes from being convex "downward" to convex "upward" in the detection period of the second-order differential signal.

Based on determining in 530 that the first local minimum point is stable (operation 530—YES), the apparatuses 100 and 200 for estimating bio-information may extract a progressive wave component based on the first local minimum point of the second-order differential signal in operation 540.

For example, the apparatuses 100 and 200 for estimating bio-information may obtain an amplitude P1 of the bio-signal, which corresponds to a time T1 of the first local minimum point, as the progressive wave component. Alternatively, the apparatuses 100 and 200 for estimating bio-information may obtain an amplitude of the bio-signal, which corresponds to an internally dividing point between the time of the first local minimum point and a time of a second local maximum point of the second-order differential signal, as the progressive wave component. In this case, a weight may be applied to each of the first local minimum point and the second local maximum point.

Based on determining that the first local minimum point is unstable (operation 530—NO), the apparatuses 100 and 200 for estimating bio-information may detect a maximum amplitude point in a systolic portion of the bio-signal, and may extract the progressive wave component based on the detected maximum amplitude point in operation 550.

For example, the apparatuses 100 and 200 for estimating bio-information may obtain an amplitude value at the maximum amplitude point as the progressive wave component. Alternatively, the apparatuses 100 and 200 for estimating bio-information may obtain, as the progressive wave component, an amplitude at an internally dividing point between a time of the inflection point detected in 530 and a time of the maximum amplitude point. In this case, a pre-defined weight may be applied to each of the time of the inflection point and the time of the maximum amplitude point, but is not limited thereto.

Next, the apparatuses 100 and 200 for estimating bio-information may estimate bio-information based on the obtained progressive wave component in operation 560. For example, the apparatuses 100 and 200 for estimating bio-information may obtain, as features, the obtained progressive wave component, i.e., an amplitude value itself, a value obtained by processing the amplitude value, a value obtained by extracting additional information from the second-order differential signal and by properly combining the extracted additional information with the progressive wave component, and the like. Further, the apparatuses 100 and 200 for estimating bio-information may estimate bio-information by applying a bio-information estimation model based on the obtained features.

Based on estimating the bio-information, the apparatuses 100 and 200 for estimating bio-information may provide the estimation result for a user. In this case, the apparatuses 100 and 200 for estimating bio-information may provide the estimated bio-information for the user by various visual/non-visual methods. In addition, the apparatuses 100 and 200 for estimating bio-information may determine the user's health condition based on the estimated bio-information, and may provide a warning or a response action for the user based on the determination.

Figure 6:
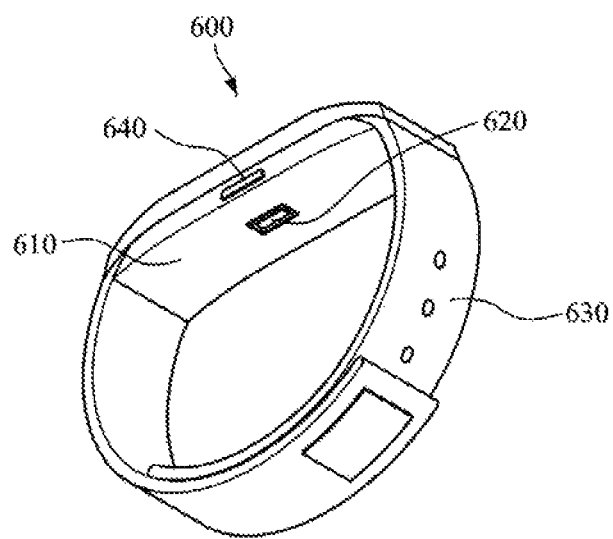
FIG. 6 is a diagram illustrating a wearable device according to an embodiment.

FIG. 6 is a diagram illustrating a wearable device according to an embodiment of the present disclosure. The aforementioned embodiments of the apparatuses 100 and 200 for estimating bio-information may be mounted in a smart watch worn on a wrist or a smart band-type wearable device, as illustrated in FIG. 6, but are not limited thereto.

Referring to FIG. 6, the wearable device 600 includes a main body 610 and a strap 630.

The main body 610 may be formed to have various shapes, and may include modules which are mounted inside or outside of the main body 610 to perform the aforementioned function of estimating bio-information and various other functions. A battery may be embedded in the main body 610 or the strap 630 to supply power to various modules of the wearable device 600.

The strap 630 may be connected to the main body 610. The strap 630 may be flexible so as to be bent around a user's wrist. The strap 630 may be bent in a manner that allows the strap 630 to be detached from the user's wrist or may be formed as a band that is not detachable. Air may be injected into the strap 630 or an airbag may be included in the strap 630, so that the strap 630 may have elasticity according to a change in pressure applied to the wrist, and the strap 630 may transmit the change in pressure of the wrist to the main body 610.

The main body 610 may include a sensor 620 for measuring a bio-signal. The sensor 620 may be mounted on a rear surface of the main body 610, which comes into contact with the upper portion of a user's wrist, and may include a light source for emitting light onto the skin of the wrist and a detector for detecting light scattered or reflected from the object. The sensor 620 may further include a contact pressure sensor for measuring contact pressure applied by the object.

A processor may be mounted in the main body 610. The processor may be electrically connected to various modules, mounted in the wearable device 600, to control operations thereof. Further, the processor may estimate bio-information by using bio-signals measured by the sensor 620.

For example, the wearable device 600 worn on the wrist measures a bio-signal from a capillary portion on an upper part of the wrist, thus acquiring a bio-signal mainly having low frequency components. Accordingly, in order to obtain features stably even in various circumstances, in which unstable bio-signals may be produced, the processor may adaptively detect a progressive wave component. For example, as described above, based on presence of an inflection point in a detection period of a second-order differential signal, the processor may determine whether a waveform of the bio-signal is stable, i.e., whether a first local minimum point of the second-order differential signal, which is generally related to the progressive wave component, is stable. Further, based on the determination on the stability, the processor may obtain a progressive wave component by using the first local minimum point of the second-order differential signal, a maximum amplitude point of the bio-signal, and the like.

In the case where the processor includes a contact pressure sensor, the processor may monitor a contact state of the object based on contact pressure between the wrist and the sensor 620, and may provide guide information on a contact position and/or a contact state for a user through a display.

Further, the main body 610 may include a storage which stores processing results of the processor and a variety of information. In this case, the variety of information may include reference information related to estimating bio-information, as well as information associated with functions of the wearable device 600.

In addition, the main body 610 may also include a manipulator 640 which receives a user's control command and transmits the received control command to the processor. The manipulator 640 may include a power button to input a command to turn on/off the wearable device 600.

A display may be mounted on a front surface of the main body 610, and may include a touch panel for receiving a touch input. The display may receive a touch input from a user, may transmit the received touch input to the processor, and may display a processing result of the processor. For example, the display may display a bio-information estimation value and warning/alarm information.

Moreover, a communication interface, provided for communication with an external device such as a user's mobile terminal, may be mounted in the main body 610. The communication interface may transmit a bio-information estimation result to an external device, e.g., a user's smartphone, to display the result to the user. However, the communication interface is not limited thereto, and may transmit and receive a variety of information.

Figure 7:
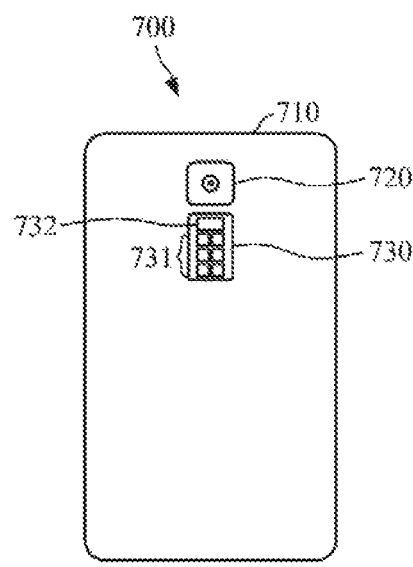
FIG. 7 is a diagram illustrating a smart device according to an embodiment.

FIG. 7 is a diagram illustrating a smart device according to an embodiment of the present disclosure. In this case, the smart device may be a smartphone, a tablet PC, and the like, and may include the aforementioned apparatuses 100 and 200 for estimating bio-information.

Referring to FIG. 7, the smart device 700 includes a main body 710 and a sensor 730 mounted on one surface of the main body 710. In this case, the sensor 730 may include a pulse wave sensor including at least one or more light sources 731 and a detector 732. As illustrated in FIG. 7, the sensor 730 may be mounted on a rear surface of the main body 710, but is not limited thereto, and may be configured in combination with a fingerprint sensor or a touch panel mounted on a front surface of the main body 710.

In addition, a display may be mounted on a front surface of the main body 710. The display may visually display a bio-information estimation result and the like. The display may include a touch panel, and may receive a variety of information input through the touch panel and transmit the received information to the processor.

Moreover, an image sensor 720 may be mounted in the main body 710. When a user's finger approaches the sensor 730 to measure a pulse wave signal, the image sensor 720 may capture an image of the finger and may transmit the captured image to the processor. In this case, based on the image of the finger, the processor may identify a relative position of the finger with respect to an actual position of the sensor 730, and may provide the relative position of the finger to the user through the display, so as to guide measurement of pulse wave signals with improved accuracy.

As described above, the processor may estimate bio-information based on bio-signals measured by the sensor 730. In this case, as described above, the processor may perform second-order differentiation on the bio-signal, may detect an inflection point in a predetermined period of the second-order differential signal, and may adaptively obtain a progressive wave component required for estimating bio-information based on the detection. In this case, as the bio-signal is measured from a user's finger by using the sensor 730 mounted on the rear surface of the smart device 700, the processor may be configured to first detect the local minimum point, and then the inflection point and a zero-crossing point, but is not limited thereto.

The embodiments of the present disclosure can be implemented by computer-readable code stored on a non-transitory computer-readable medium. The computer-readable medium may be any type of recording device in which data is stored in a computer-readable manner.

Examples of the computer-readable medium include a ROM, a RAM, a CD-ROM, a magnetic tape, a floppy disc, an optical data storage, and a carrier wave (e.g., data transmission through the Internet). The computer-readable medium can be distributed over a plurality of computer systems connected to a network so that a computer-readable code is written thereto and executed therefrom in a decentralized manner. Functional programs, code, and code segments for implemented the embodiments of the present disclosure can be=deduced by programmers of ordinary skill in the art, to which the present disclosure pertains.

The present disclosure has been described herein with regard to various embodiments. However, it will be obvious to those skilled in the art that various changes and modifications can be made without changing technical ideas and features of the present disclosure. Thus, it is clear that the above-described embodiments are illustrative in all aspects and are not intended to limit the present disclosure.

What is claimed is:

1. An apparatus for estimating bio-information, the apparatus comprising:
    a sensor configured to obtain a bio-signal from an object;
    a processor; and
    an output interface;
    wherein the processor is configured to:
        obtain a second-order differential signal of the bio-signal;
        determine whether a first local minimum point of the second-order differential is stable or unstable;
        based on determining that the first local minimum point of the second-order differential signal is stable, extract a progressive wave component from the bio-signal using the first local minimum point of the second-order differential signal,
        based on determining that the first local minimum point of the second-order differential signal is unstable, extract the progressive wave component from the bio-signal using a maximum amplitude point in a systolic portion of the bio-signal;
        determine the estimated bio-information based on the extracted progressive wave component, the estimated bio-information representing an actual health condition of a user having the object; and
        direct the output interface to provide the estimated bio-information to the user so as to monitor the actual health condition.

2. The apparatus of claim 1, wherein the sensor comprises a pulse wave sensor including a light source configured to emit light onto the object, and a detector configured to detect light reflected by or scattered from the object.

3. The apparatus of claim 1, wherein the processor is further configured to:
    determine whether an inflection point exists in a detection period of the second-order differential signal; and
    determine whether the first local minimum point is stable based on whether the inflection point exists in the detection period of the second-order differential signal.

4. The apparatus of claim 3, wherein the detection period comprises a time interval between a first local maximum point and the first local minimum point of the second-order differential signal.

5. The apparatus of claim 3, wherein the inflection point is a point at which a waveform of the second-order differential signal changes from being convex downward to convex upward.

6. The apparatus of claim 5, wherein the processor is further configured to:
    obtain a fourth-order differential signal of the bio-signal;
    detect a first point, which satisfies a condition that an amplitude at the first point is greater than zero and an amplitude at a second point is less than zero, in a detection period of the fourth-order differential signal; and
    detect a point, corresponding to the first point, as the inflection point from the second-order differential signal.

7. The apparatus of claim 1, wherein the processor is configured to extract, as the progressive wave component, at least one of an amplitude of the bio-signal, which corresponds to a time of the first local minimum point, and an amplitude of the bio-signal which corresponds to an internally dividing point between the time of the first local minimum point and a time of a second local maximum point of the second-order differential signal.

8. The apparatus of claim 1, wherein based on determining that the first local minimum point is unstable, the processor is further configured to detect the maximum amplitude point in the systolic portion of the bio-signal.

9. The apparatus of claim 8, wherein the processor is configured to extract, as the progressive wave component, at least one of an amplitude of the maximum amplitude point, and an amplitude of the bio-signal which corresponds to an internally dividing point between a time of the inflection point, which is detected in the detection period of the second-order differential signal, and a time of the maximum amplitude point.

10. The apparatus of claim 1, wherein the estimated bio-information comprises at least one of blood pressure, vascular age, arterial stiffness, aortic pressure waveform, stress index, and fatigue level.

11. The apparatus of claim 1,
wherein the sensor is a bio-signal sensor,
wherein the apparatus further comprises:
an image sensor, and
a display,
wherein the image sensor is configured to capture an image of the object and transmit the image to the processor, and
wherein the processor is further configured to, based on the image:
identify a relative position of the object with respect to an actual position of the bio-signal sensor, and
display the relative position of the objet on the display so as to guide measurement of the bio information with improved accuracy.

12. A method of estimating bio-information, the method comprising:
obtaining a bio-signal from an object;
obtaining a second-order differential signal of the bio-signal;
determining whether a first local minimum point of the second-order differential signal is stable or unstable;
based on determining that the first local minimum point of the second-order differential signal is stable, extracting a progressive wave component using the first local minimum point of the second-order differential signal,
based on determining that the first local minimum point of the second-order differential signal is unstable, extracting the progressive wave component from the bio-signal using a maximum amplitude point in a systolic portion of the bio-signal;
determining the estimated bio-information based on the extracted progressive wave component, the estimated bio-information representing an actual health condition of a user having the object; and
directing an output interface to provide the estimated bio-information to the user so as to monitor the actual health condition.

13. The method of claim 12, wherein the determining whether the first local minimum point of the second-order differential signal is stable comprises:

determining whether an inflection point exists in a detection period of the second-order differential signal; and
determining whether the first local minimum point is stable based on whether the inflection point exists in the detection period of the second-order differential signal.

14. The method of claim 13, wherein the detection period comprises a time interval between a first local maximum point and the first local minimum point of the second-order differential signal.

15. The method of claim 13, wherein the inflection point is a point at which a waveform of the second-order differential signal changes from being convex downward to convex upward.

16. The method of claim 15, wherein the detecting of the inflection point comprises:
obtaining a fourth-order differential signal of the bio-signal;
detecting a first point, which satisfies a condition that an amplitude at the first point is greater than zero and an amplitude at a second point is less than zero, in a detection period of the fourth-order differential signal; and
detecting a point, corresponding to the first point, as the inflection point from the second-order differential signal.

17. The method of claim 12, wherein the extracting of the progressive wave component comprises, in response to determining that the first local minimum point is stable, extracting, as the progressive wave component, at least one of an amplitude of the bio-signal, which corresponds to a time of the first local minimum point, and an amplitude of the bio-signal which corresponds to an internally dividing point between the time of the first local minimum point and a time of a second local maximum point of the second-order differential signal.

18. The method of claim 12, wherein the extracting of the progressive wave component comprises:
in response to determining that the first local minimum point is unstable, detecting the maximum amplitude point in the systolic portion of the bio-signal.

19. The method of claim 18, wherein the extracting of the progressive wave component based on the detected maximum amplitude point comprises extracting, as the progressive wave component, at least one of an amplitude of the maximum amplitude point, and an amplitude of the bio-signal which corresponds to an internally dividing point between a time of the inflection point, which is detected in the detection period of the second-order differential signal, and a time of the maximum amplitude point.

20. The method of claim 12, further comprising;
obtaining an image of the object;
identifying a relative position of the object with respect to an actual position of a bio-signal sensor; and
direct a display to display the relative position of the object so as to guide measurement of the bio information with improved accuracy,
wherein the obtaining the bio-signal from the object is done via the bio-signal sensor.

* * * * *